US008216829B2

(12) United States Patent
Ouazzani et al.

(10) Patent No.: US 8,216,829 B2
(45) Date of Patent: Jul. 10, 2012

(54) DEVICE FOR CULTURE OF CELLS OR MICRO-ORGANISMS

(75) Inventors: Jamal Ouazzani, Massy (FR); Sylvie Cortial, Les Ulis (FR); Didier Sergent, Bretigny sur Orge (FR); Philippe Lopes, St Maurice Montcouronne (FR)

(73) Assignee: Centre National de la Recherche Scientifique (CNRS), Paris (FR)

( * ) Notice: Subject to any disclaimer, the term of this patent is extended or adjusted under 35 U.S.C. 154(b) by 544 days.

(21) Appl. No.: 12/227,472

(22) PCT Filed: May 18, 2007

(86) PCT No.: PCT/EP2007/054834
§ 371 (c)(1),
(2), (4) Date: Mar. 20, 2009

(87) PCT Pub. No.: WO2007/135098
PCT Pub. Date: Nov. 29, 2007

(65) Prior Publication Data
US 2009/0305396 A1    Dec. 10, 2009

(30) Foreign Application Priority Data
May 19, 2006  (FR) ...................................... 06 04525

(51) Int. Cl.
*C12M 1/00* (2006.01)
*C12M 3/00* (2006.01)
*C12M 1/02* (2006.01)

(52) U.S. Cl. ............... 435/303.1; 435/289.1; 435/303.3; 435/294.1; 435/809

(58) Field of Classification Search ............... 435/289.1, 435/303.1, 303.3, 294.1, 809
See application file for complete search history.

(56) References Cited

U.S. PATENT DOCUMENTS

| 3,562,114 A * | 2/1971 | Steidl ............................. 312/236 |
| 4,212,949 A   | 7/1980 | Kozhemyakin et al. |
| 6,593,136 B1 * | 7/2003 | Geiss ............................. 435/325 |

FOREIGN PATENT DOCUMENTS

| BE | 737189 A | 2/1970 |
| DE | 40 28 871 A1 | 3/1992 |
| DE | 4443902 C1 | 4/1996 |
| GB | 1360968 | 7/1974 |
| JP | 11089556 A | 4/1999 |
| WO | WO-9404273 A1 | 3/1994 |
| WO | WO-00/29544 | 5/2000 |

* cited by examiner

*Primary Examiner* — William H Beisner
*Assistant Examiner* — Danielle Henkel
(74) *Attorney, Agent, or Firm* — Blakely, Sokoloff, Taylor & Zafman

(57) ABSTRACT

This invention relates to a device intended for the culture of cells or micro-organisms, characterised by the fact that it comprises a chamber (100) composed of a tank (110) and a lid (150), adapted so that when in the closed state, it defines a sealed volume under a controlled pressure, and an assembly (200) designed to be placed inside the chamber (100), while being removable from it when the lid (150) is opened, said assembly comprising (200) a support frame (210) and a plurality of plates (250) carried by the support frame (210), the chamber (100) also comprising means designed to successively sterilise its content, for seeding a culture medium placed in the trays (250) and a means for controlling the atmosphere in the chamber (100), to enable the culture of cells or micro-organisms.

23 Claims, 3 Drawing Sheets

Figure 7:
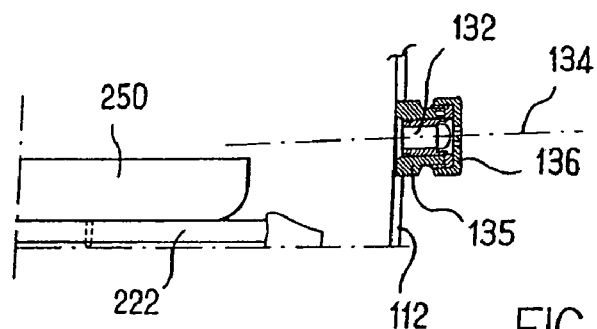

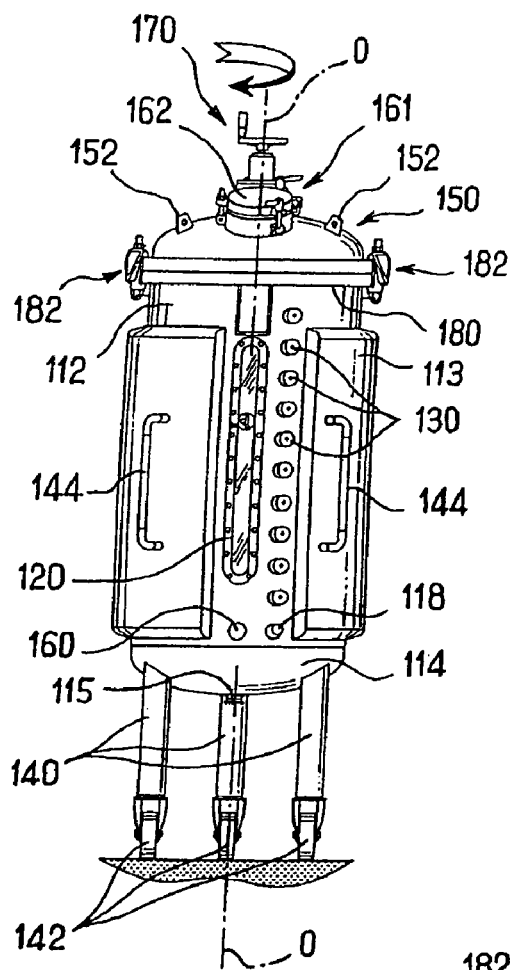
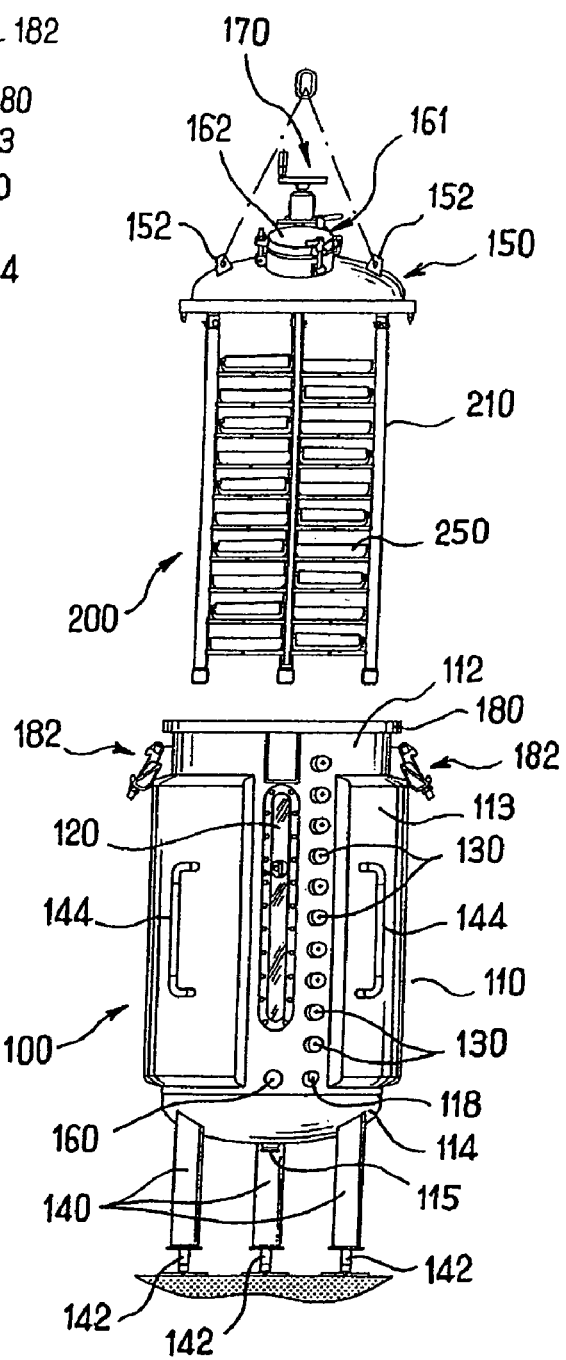

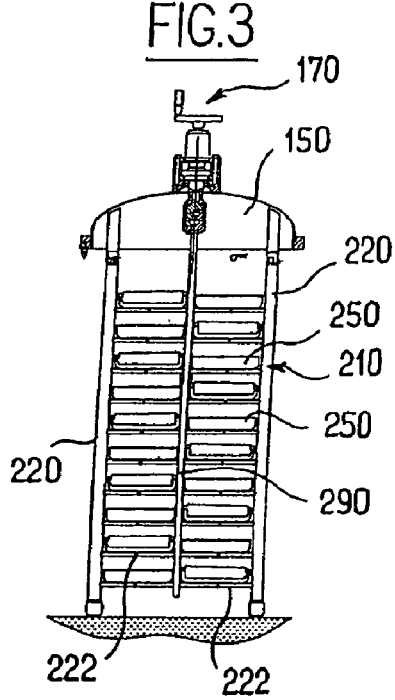
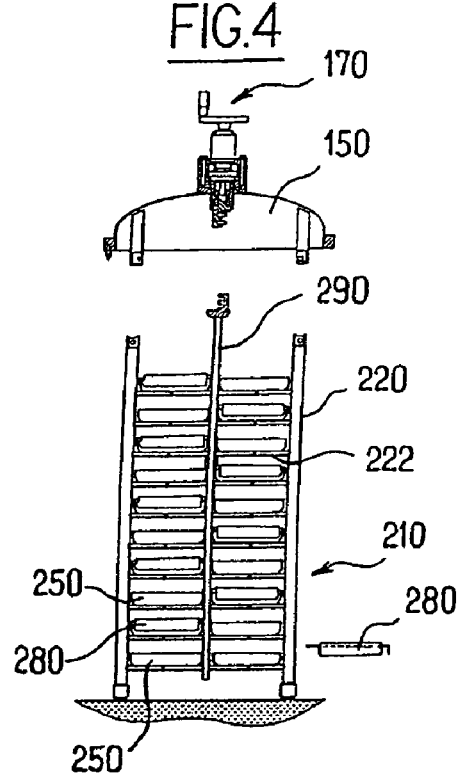
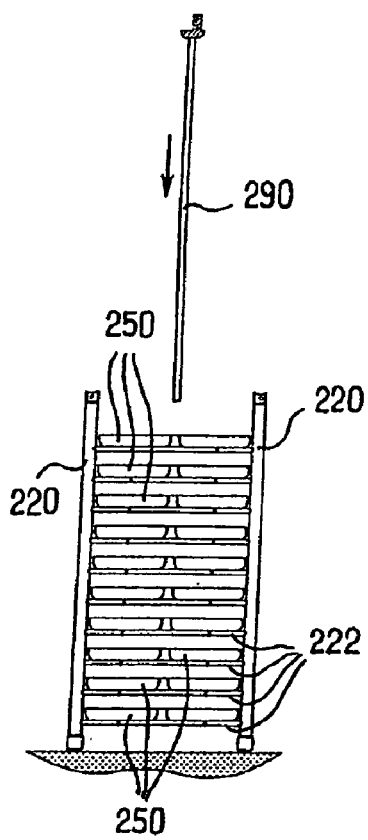
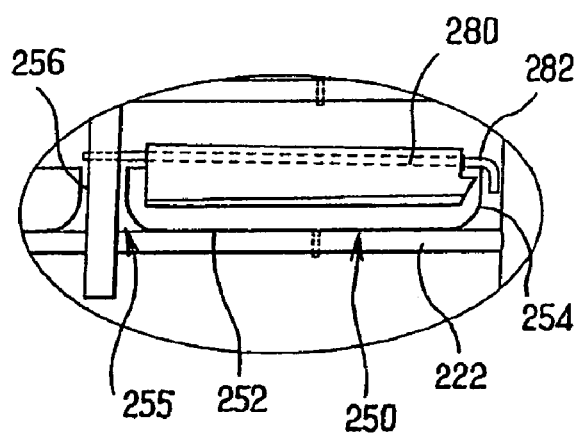

DEVICE FOR CULTURE OF CELLS OR MICRO-ORGANISMS

The present application is a Utility claiming the benefit of Application No. PCT/EP2007/054834, filed May 18, 2007.

The present invention relates to the field of the culture of cells. It applies in particular to the culture of micro-organisms. However, it is not limited to this particular application and extends to the culture of any cell type (plant cells, insect cells or even animal cells).

The person skilled in the art knows in particular that the research and development of molecules of interest, starting from natural substances, is a major challenge in the therapeutic field.

This research requires equipment allowing the culture of micro-organisms.

Many items of equipment for this purpose have already been proposed.

One example of a known item of equipment is described in the document EP-A-1131404. This item of equipment has limits. In particular, it does not allow culture in a liquid medium, which rules out the culture of insect cells or animal cells.

However, none of the known items of equipment as yet gives complete satisfaction, in particular by adapting to different cell types, by allowing cultures on supports of the nutrient agar type and by combining the different steps of a cell culture.

In this context, the object of the present invention is to propose a new item of equipment which makes it possible to improve the situation.

This object is achieved according to the present invention by a device intended for the culture of cells or micro-organisms, characterised in that it comprises a chamber composed of a tank and a lid, adapted so as to define in the closed state a sealed volume under a controlled pressure, and an assembly designed to be placed inside the chamber while being capable of being removed therefrom when the lid is opened, said assembly comprising a support frame and a plurality of plates carried by the support frame, the chamber also comprising means for successively sterilising the contents thereof, seeding a culture medium placed in the plates and controlling the atmosphere of the chamber so as to allow the culture of cells or micro-organisms.

As will be explained in more detail below, the structure thus proposed according to the present invention makes it possible to carry out all the essential steps for the culture of micro-organisms within the chamber. The present invention thus makes it possible to avoid any contamination before and during the culture.

According to another advantageous feature of the invention, the present invention also comprises means designed to carry out a treatment after the culture, preferably a heat treatment capable of drying the culture medium and also the cultured micro-organisms.

According to another advantageous feature of the present invention, the interface defined between the tank and the lid of the chamber is an interface comprising an annular seal.

According to another advantageous feature of the present invention, the support frame is connected to the lid of the chamber.

According to another advantageous feature of the present invention, the chamber is designed to control a stream of gas injected into the tank, in particular a stream of steam, air, oxygen or any other gas which performs the culture in an optimal manner, without any risk of entrainment of micro-organisms.

Figure 9:
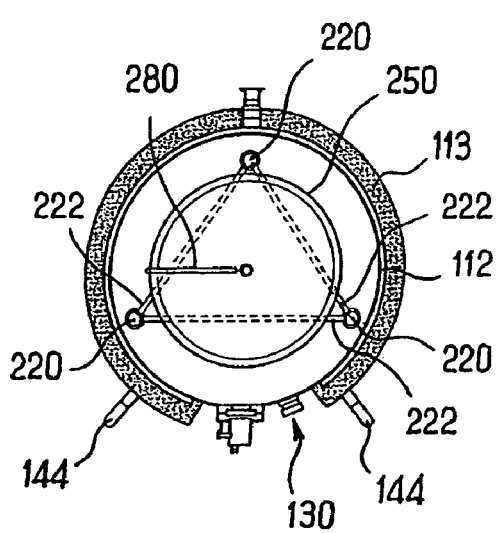
Figure 8:
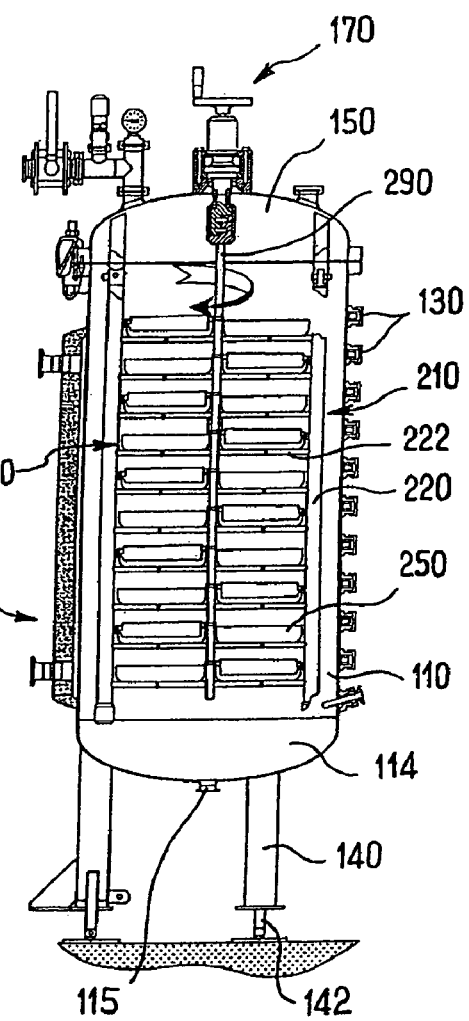

Other features, objects and advantages of the present invention will become apparent on reading the following detailed description with reference to the appended drawings, which are given by way of non-limiting examples and in which:

FIG. 1 shows a schematic external view of a device according to the present invention, FIG. 2 shows the extraction of the assembly consisting of a support frame and plates out of the tank when the lid is opened, FIGS. 3, 4 and 5 show three steps of disassembling said assembly so as to gain access to the plates, FIG. 6 shows a side view of a blade used to homogenise the medium carried by a plate, or to spread a pre-culture over the latter, FIG. 7 schematically shows means provided on the tank for seeding the plates, FIG. 8 shows a schematic view, partially in vertical section, of the device according to the present invention, and FIG. 9 shows a schematic view in horizontal section of the same device.

As mentioned above, the device according to the present invention is composed essentially of a chamber 100 and an extractable assembly 200.

The chamber 100 is composed of a tank 110 and a lid 150.

The assembly 200 is composed of a support frame 210 and plates 250.

The chamber 100 has a general symmetry of revolution about a vertical axis O-O.

The tank 110 consists of a cylindrical wall 112 of revolution about the axis O-O, closed at its base by a dome 114 which is concave towards the outside and is typically substantially semispherical.

Preferably, over almost its entire height, the cylindrical wall 112 is covered on the exterior by an annular enclosure 113 forming a double casing. Such an enclosure makes it possible, when it is supplied with a fluid at a controlled temperature, to control in a homogeneous manner the temperature of the internal volume of the chamber.

This temperature control may be used, of course by adapting and changing the temperature of the fluid supplying the enclosure 113, in all of the steps carried out, namely sterilisation, seeding, culture, or even a subsequent step, in particular drying.

More specifically, as can be seen in the appended figures, preferably the annular enclosure 113 does not cover the entire periphery of the tank 112. The annular enclosure 113 has a C-shaped horizontal section which covers approximately 310 to 320° around the wall 112.

In the free space defined between the two peripheral ends of the annular enclosure 113, that is to say the space where the wall 112 is directly accessible, the latter is preferably provided with a window 120 and with means 130 designed to seed a culture medium carried by the plates 250. The window 120 thus preferably has an oblong shape, the large dimension of which extends vertically over the entire height of the wall 112 facing the plates 250.

The means 130 may be the subject of different variants. They are preferably formed by stoppers 132 made from elastomeric material or the like which can be passed through by suitable needles, the latter themselves being connected outside the chamber to a seeding source, so as to carry out a controlled seeding with micro-organisms of a culture medium carried by the plates 250. For this, the end of said needles located inside the chamber must be located above the plates 250, and preferably on a zone controlled with precision. These needles or needles of different length also make it possible to add any solution to the plates and also to remove in a sterile manner by suction all or part of the contents of the plate.

Such a control can be carried out on the one hand visually by means of the window 120. This is because, as can be seen in FIGS. 1 and 2, the window 120 is adjacent to the means 130. On the other hand, this control can be carried out by taking care to control with precision the length of the needles introduced into the chamber, for example by monitoring the position of a reference mark provided on the needles with respect to the stopper 130.

As can be seen in FIG. 7, preferably each means 130 comprises an elastomeric block 132 which is generally cylindrical of revolution about an axis 134 which is generally radial with respect to the axis O-O but slightly inclined downwards with respect to the horizontal as it approaches the axis O-O. The elastomeric blocks 132 are advantageously placed in a cage 135 associated with a removable ring 136 which makes it possible to replace the blocks 132 after several uses.

The person skilled in the art will understand that such stoppers 130, made from elastomeric material, automatically seal the chamber when the needle is removed.

There is provided a number of means 130, distributed over the height of the tank 110, equal to the number of plates 250 carried by the support frame 210.

Of course, as a variant, it would be possible to provide an annular enclosure 113 covering the entire periphery of the wall 112 and to therefore place the window 120 and the means 130 on this enclosure 113 while ensuring the sealing at this point.

The lower dome 114 is preferably mounted on a set of feet 140, typically three feet 140, which are each provided with a wheel 142 at their base. This arrangement makes it possible to display the device with ease, for example between a site of loading and unloading the assembly 200 (as shown schematically in FIG. 2), requiring a large height, and a site of culture or storage, in the closed state (as shown schematically in FIG. 1), which allows a smaller installation height.

To facilitate this displacement, the tank 110 is preferably equipped with handles 144, located for example on the exterior of the annular enclosure 113.

Preferably, the dome 114 comprises at its base a drainage orifice 115 which is closed off by any suitable means capable of opening on demand.

Depending on the type of culture and the culture process used, the dome 114 may receive in its internal volume a fluid which participates in the control of the internal atmosphere of the chamber.

The orifice 115 makes it possible to drain such a fluid with ease, or even to remove for any analyses a simple of this fluid.

The tank 112 also has at least one inlet 160 which makes it possible to inject a suitable fluid or gas (oxygen, compressed air, steam, etc.) during the steps of sterilisation, seeding, culture, or any other step, in particular during any subsequent treatment by drying. The inlet 160 is preferably provided in the lower part of the wall 112, close to the dome 114.

The appended figures show a device which also comprises a temperature probe 118, designed to measure the internal temperature of the chamber, carried by the wall 112 close to the dome 114.

Such a probe 118 may be replaced by any suitable means, for example, and without any limitation, temperature measurement means suitable for being placed within the culture medium carried by the plates 250. In this case, preferably, these temperature means are of the wireless transmission type.

As can be seen in the appended figures, the tank 110 is equipped in its upper part with a collar 180 which serves for supporting the lid 150 and a series of means 182 suitable for locking the lid 150 in a sealed and pressurised manner. Such means 182, which are conventional per se, will not be described in detail below.

The lid 150 is formed essentially of an outwardly convex dome, symmetrical to the dome 114, that is to say substantially semispherical.

A seal, not shown in detail in the appended figures, may be embodied in any suitable manner and is inserted between the collar 180 of the tank 112 and the periphery of the base of the lid 150. The person skilled in the art will note that the present invention thus defines an annular interface of simple configuration which makes it possible to ensure both perfect sealing and perfect integrity or sterilisation, which would not be obtained with means for opening a chamber of the pivoting door type which require hinges or the like, the sealing and sterilisation of which are complex to achieve.

The lid 150 has several attachment points 152 making it possible to raise the lid, and if necessary the assembly 200, by means of a hoist or the like.

As can be seen in the figures, the lid 250 has an access means of the manhole type or the like 161 comprising a hatch 162 capable of opening on demand and closing in a sealed manner.

The lid 150 may be equipped with other accessories. The appended figures show in particular a means 170 centred on the axis O-O and capable of driving in rotation on demand a rod 290 making it possible to drive blades 280 in rotation.

Such means 170 may be formed of manual drive means comprising a crank as shown in the appended figures, or of motor drive means associated with programming making it possible to control the speed, duration and sequences of rotation.

The lid 150 may be equipped with illumination means making it possible to illuminate selectively the internal volume of the chamber, for example during the loading or seeding sequences or even if necessary throughout the entire culture of the micro-organisms. It may also comprise means for observing the interior of the tank. In the case where the tank 110 is made from stainless steel, its inner surface forms a reflector allowing a good homogeneity of illumination of the entire internal volume of the chamber from one limited source carried by the lid. Where necessary, an illumination system may also be provided at the window so as to make it easier to observe the internal volume of the chamber. Such an illumination means may be formed by a ramp extending over the entire height of the window 120 or by a source of limited sections which is mounted so as to move in translation, preferably on the exterior of the tank 110, along the window 120 so as to selectively illuminate one of the plates 250.

The support frame 210 may form the subject of many variants. It is preferably composed of a plurality of vertical columns 220, typically three columns 220 distributed at equal angles, connected to one another by sets of crossbars or horizontal bars 222 serving to support the plates 250.

According to the non-limiting embodiment shown in the appended figures, the bars 222 define ten superposed levels, each designed to receive one receiving plate 250.

The extraction of the frame 210 and of the plates 250 carried by the latter may take place by any suitable means, for example by connecting the upper ends of the columns 220 to a hoist, after removing the lid 150. Preferably however, as shown in FIGS. 3 to 5, means of connection between the upper ends of the columns 220 and the lid 150 are provided, for example based on pins or the like. The extraction of the support frame 210 and of the plates 250 thus takes place when the lid 150 is raised, as can be seen in FIG. 2.

It will be noted that, advantageously, the means of connection between the upper ends of the columns 220 and the lid 150 are removable means which make it possible to separate the support frame 220 and the lid 150, as can be seen in FIG. 4.

Each plate 250 is preferably generally cylindrical of revolution. It comprises a circular flat base 252 surmounted at its periphery by a cylindrical skirt 254. The height of the skirts 254 may be variable. It typically has a height of around 5 cm for a plate diameter of around 50 cm. Such a plate structure is suitable for receiving any type of culture medium, solid, semi-solid or liquid, although the present invention is preferably dedicated to a culture on a medium of the nutrient agar type.

The person skilled in the art will appreciate that the dimensions and number of plates mentioned above, which are of course not limiting, allow a simultaneous culture over a surface area of around 2 m², much greater than the surface areas allowed by the most conventional devices available to date, in particular in the form of Petri dishes.

Preferably, the device according to the present invention is also equipped with means designed to homogenise the culture medium and/or the seeding thereof. These means may form the subject of many variants. They are preferably formed by blades or scrapers 280 carried respectively by secondary rods 282 which extend radially with respect to the main vertical rod 290 described above.

Of course, there is thus provided at least one rod 282 and at least one associated blade 280, distributed over the length of the rod 290, for each of the plates 250. As can be seen in FIG. 6, the radially outer free end of the rods 282 may rest on the upper rim of the skirts 254 of the plates 250 so as to ensure a precise positioning of the blades 280 with respect to the plates 250.

The blades 280 may be fixed in position on the rods 282. However, they are preferably mounted such that they can pivot freely on these rods 282, about the longitudinal axis of the latter, so as to sweep the surface of the culture medium, without penetrating the latter.

Where necessary, the blades 280 described above for spreading the seeding material over the surface of the culture medium may be replaced by stirring means. In this case, means replacing the blades 280 are connected rigidly to the support rod 182 without any possibility of rotation with respect to the longitudinal axis of the latter.

As can be seen in the appended figures, the presence of the means 290, 282, 280 requires that the main rod 290 passes through the plates 250. For this, the plates 250 also have in their centre an orifice 255 surmounted by a cylindrical skirt 256 of the same height as the outer peripheral skirt 254.

In order to remove the plates 250, the procedure is essentially as follows once the lid 150 and the support frame 210 have been removed. The lid 150 is separated from the support frame 210 (FIG. 4). Preferably, the blades 280 and the support rods 282 are separated from the main rod 290 (FIG. 4). Finally, the rod 290 is removed in the upward direction (FIG. 5). The plates 250 can then be removed by horizontal translation.

As a variant, it may be provided that each plate 250 has a radial groove in its base 252 connecting the central orifice 255 to the outer periphery of the plate. This arrangement allows a removal of each plate 250 without having to remove the vertical rod 290. Of course, in this case, the radially inner skirt 256 does not cover 360°. It is connected to the radially outer skirt 254 by two vertical walls, of the same height as said skirts, said walls being straight and framing said groove.

Preferably, all of the means which constitute the chamber 100 and the assembly 200 are made from metal, advantageously from stainless steel.

Preferably, the internal volume of the chamber is around 500 liters.

The person skilled in the art will understand that the present invention makes it possible to carry out in a confined environment, thereby making it possible to avoid any contamination, all of the steps of sterilisation, seeding and culture. However, the device according to the present invention is not limited to carrying out these steps. It also allows in particular post-culture steps, for example steps of drying, neutralisation, etc., typically while controlling the internal temperature of the chamber within a temperature range from 4 to 120° C.

The present invention also makes it possible to culture simultaneously in the chamber, on respective different plates, different cells or micro-organisms. To this end, in order to avoid any contamination of one culture by a cell from another plate, the chamber is designed to control a stream of gas injected into the tank, in particular a stream of oxygen, so that this stream performs the culture in an optimal manner, without any superfluous additional stream likely to entrain or displace micro-organisms within the chamber.

Of course, all of the fluid and gas extracted from the chamber is preferably filtered in order to avoid any contamination of the environment.

Furthermore, all the inlets and outlets of the chamber capable of switching between two types of fluid or gas are preferably equipped with double or multiple valves so as to ensure the synchronisation between the operations of switching the different fluids and gases.

Of course, the present invention is not limited to the particular embodiments which have just been described, but rather extends to all variants in accordance with its spirit.

In particular, the chamber may carry any additional equipment (manometer, inlet or outlet valves, filters, probes, etc.) as shown schematically in FIG. 8 by way of non-limiting example, for monitoring the correct operation of the device.

The invention claimed is:

1. Device for the culture of cells or micro-organisms, comprising:
    a chamber (100) composed of a tank (110) and a lid (150), adapted so as to define in the closed state a sealed volume under a controlled pressure, and an assembly (200) designed to be placed inside the chamber (100) while being capable of being removed therefrom when the lid (150) is opened, wherein said assembly (200) further comprises a support frame (210) and a plurality of plates (250) carried by the support frame (210), the chamber (100) also comprising means (113, 160, 130, 114) for successively sterilising the contents thereof, seeding a culture medium placed in the plates (250) and controlling the atmosphere of the chamber (100) so as to allow the culture of cells or micro-organisms, and wherein the device comprises means (280) for homogenising comprises rods (282) of which one free end rests on a skirt (256) of the plates (250).

2. Device according to claim 1 further comprising means (113) designed to carry out a treatment after the culture, preferably a heat treatment capable of drying the culture medium and also the cultured cells or micro-organisms.

3. Device according to one of claims 1 or 2, wherein the interface defined between the tank (110) and the lid (150) of the chamber (100) is an interface comprising an annular seal.

4. Device according to claim 1, wherein the support frame (210) is connected to the lid (150) of the chamber (100), preferably by removable connecting means.

5. Device according to claim 1, wherein the chamber (100) is designed to control a stream of gas injected into the tank, in particular a stream of oxygen, so that this stream performs the culture in an optimal manner, without any additional stream likely to entrain cells or micro-organisms.

6. Device according to claim 1, wherein the tank (110) comprises a double casing (113) defining an enclosure which, when it is supplied with a fluid at a controlled temperature, makes it possible to control in a homogeneous manner the temperature of the internal volume of the chamber (100).

7. Device according to claim 1, wherein the chamber (100) comprises a window (120) extending over the entire height of the assembly (200) comprising plates (250).

8. Device according to claim 1, wherein the chamber (100) comprises means (130) allowing the introduction of needles for seeding a culture medium or removing all or part of the contents of the plates.

9. Device according to claim 8, wherein the means (130) allowing the introduction of needles are formed by stoppers (132) made from elastomeric material.

10. Device according to claim 9, wherein the stoppers (132) made from elastomeric material are mounted in a removable manner.

11. Device according to claim 1, wherein the chamber (100) comprises a number of means (130) allowing the introduction of needles for seeding a culture medium, equal to the number of plates (250) carried by the support frame.

12. Device according to claim 1, wherein the chamber (100) has a drainage orifice (115) at its base.

13. Device according to claim 1, wherein the chamber (100) comprises at least one inlet (160) making it possible to inject a suitable fluid or gas.

14. Device according to claim 1, wherein the chamber (100) comprises probes dedicated to controlling all the parameters inside the tank, and at least one temperature probe (118) for measuring the internal temperature of the chamber.

15. Device according to claim 1, wherein the chamber (100) comprises temperature measurement means suitable for being placed within the culture medium carried by the plates (250).

16. Device according to claim 1, wherein the chamber (100) comprises temperature measurement means of the wireless transmission type.

17. Device according to claim 1, wherein it comprises means for illuminating the internal volume of the chamber (100).

18. Device according to claim 1, wherein the lid (150) of the chamber (100) carries means for illuminating and observing the interior of the tank.

19. Device according to claim 1, wherein it comprises illumination means at a window (120).

20. Device according to claim 1, wherein the support frame (210) is composed of a plurality of vertical columns (220), connected to one another by sets of crossbars or horizontal bars (222) serving to support the plates (250).

21. Device according to claim 1, wherein the means (280) designed to homogenise the culture medium and/or the seeding thereof comprise blades or spreaders (280) capable of being driven in rotation.

22. Device according to claim 1, wherein the plates (250) have in their centre an orifice (255) surmounted by a cylindrical skirt (256) allowing the passage of a rod (290) designed to drive the homogenisation means.

23. Device according to claim 1, wherein each plate (250) has a radial groove.

* * * * *